US009652589B2

(12) United States Patent
Caspi (10) Patent No.: US 9,652,589 B2
(45) Date of Patent: May 16, 2017

(54) SYSTEMS AND METHODS FOR USING A TOUCH-SENSITIVE DISPLAY UNIT TO ANALYZE A MEDICAL IMAGE

(71) Applicant: General Electric Company, Schenectady, NY (US)

(72) Inventor: Amit Caspi, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 1087 days.

(21) Appl. No.: 13/728,151

(22) Filed: Dec. 27, 2012

(65) Prior Publication Data

US 2014/0189560 A1   Jul. 3, 2014

(51) Int. Cl.
G06F 19/00   (2011.01)

(52) U.S. Cl.
CPC ............ *G06F 19/32* (2013.01); *G06F 19/321* (2013.01); *G06F 19/3406* (2013.01)

(58) Field of Classification Search
None
See application file for complete search history.

(56) References Cited

U.S. PATENT DOCUMENTS

| 5,964,707 | A * | 10/1999 | Fenster ............... A61B 8/4209 600/443 |
| 8,013,839 | B2 | 9/2011 | Ording et al. |
| 8,543,415 | B2 * | 9/2013 | Venon et al. ................. 705/2 |
| 2003/0212327 | A1 * | 11/2003 | Wang ................... A61B 6/463 600/437 |
| 2006/0267927 | A1 * | 11/2006 | Crenshaw et al. ............. 345/156 |
| 2008/0094356 | A1 * | 4/2008 | Ording ................ G06F 3/04886 345/157 |
| 2009/0043195 | A1 * | 2/2009 | Poland ..................... A61B 8/00 600/437 |
| 2009/0138800 | A1 * | 5/2009 | Anderson et al. ............. 715/702 |
| 2010/0004539 | A1 * | 1/2010 | Chen ................... A61B 8/0825 600/445 |
| 2010/0222671 | A1 * | 9/2010 | Cohen ................... G06T 7/0022 600/424 |

(Continued)

OTHER PUBLICATIONS

Tim Carmody; Ostylus Gives Touchscreen Drawing Jewelers' Precision; oStylus Touchscreen Drawing Jewerlers Precision | Wired; Nov. 2010; 2 pages.

*Primary Examiner* — Maryam Ipakchi
(74) *Attorney, Agent, or Firm* — Dean D. Small; The Small Patent Law Group, LLC (57) ABSTRACT

A user interface including a touch-sensitive display unit that has a display area and is configured to show a medical image and a user-selectable element on the display area. The display unit is configured to detect an operator touch and detect a location of the operator touch in the display area. The user-selectable element includes an activating portion and a location indicator. The display unit is configured to move the user-selectable element along the medical image as directed by the operator when the activating portion is touched. The location indicator and the activating portion have fixed positions with respect to each other as the user-selectable element is moved along the display area. The user-selectable element is configured to operate in an activated state and in an inactivated state. The user-selectable element configured to modify the medical image when in the activated state.

20 Claims, 8 Drawing Sheets

(56) References Cited

U.S. PATENT DOCUMENTS

| | | | |
|---|---|---|---|
| 2010/0295796 A1 | 11/2010 | Roberts et al. | |
| 2011/0074677 A1* | 3/2011 | Ording | G06F 3/04886 345/158 |
| 2013/0324850 A1* | 12/2013 | Petruzzelli et al. | 600/443 |
| 2014/0059486 A1* | 2/2014 | Sasaki | G01S 7/52084 715/810 |
| 2014/0187948 A1* | 7/2014 | Gerard et al. | 600/443 |

\* cited by examiner

SYSTEMS AND METHODS FOR USING A TOUCH-SENSITIVE DISPLAY UNIT TO ANALYZE A MEDICAL IMAGE

BACKGROUND

The subject matter disclosed herein relates generally to systems and methods that enable a user to interact with, analyze, or modify a medical image, and more particularly to systems and methods that include a touch-sensitive display unit.

Patients can be imaged using a wide variety of different imaging technologies. Medical imaging systems may include ultrasound imaging systems, magnetic resonance imaging (MRI) systems, computer tomography (CT) systems, positron emission tomography (PET) systems, single photon emission computed tomography (SPECT) systems, x-ray imaging systems, and others. The medical images include a region-of-interest (ROI) of the patient, e.g., heart, lung, brain, or whole body. The ROI may include anatomical features that are analyzed by healthcare provides or other qualified professionals to diagnose a medical condition.

On some occasions, it may be desirable to analyze the medical images to select certain anatomical features in the medical image for further analysis and/or to obtain measurements of the anatomical features. For example, ultrasound images of the heart (also called echocardiograms or "echos") may show anatomical structures (e.g., ventricles, atria, valves, septum, and the like) as well as blood flow through the heart. Such images of the heart may be used to measure dimensions of designated cardiac structures to diagnose a medical condition. For example, cardiovascular mortality and morbidity increases with increasing values of left ventricular mass. Accordingly, it is desirable to have diagnostic systems that can determine the left ventricular mass.

In some known diagnostic systems, an operator of the system may use an input device to select the anatomical features for further analysis and/or to measure the anatomical features. The input devices typically include a keyboard, mouse, touchpad, and the like. Such input devices, however, may require additional space for the diagnostic system and may complicate the usability of the diagnostic system.

BRIEF DESCRIPTION

In one embodiment, a user interface is provided that includes a touch-sensitive display unit that has a display area and is configured to show a medical image and a user-selectable element on the display area. The display unit is configured to detect an operator touch and detect a location of the operator touch in the display area. The user-selectable element includes an activating portion and a location indicator. The display unit is configured to move the user-selectable element along the medical image as directed by the operator when the activating portion is touched. The location indicator and the activating portion have fixed positions with respect to each other as the user-selectable element is moved along the display area. The user-selectable element is configured to operate in an activated state and in an inactivated state. The user-selectable element configured to modify the medical image when in the activated state.

In another embodiment, a method of using a touch-sensitive display unit is provided that includes displaying a medical image and a user-selectable element in a display area of the display unit. The user-selectable element includes an activating portion and a location indicator. The user-selectable element is configured to move along the medical image when the activating portion is touched and directed by the operator. The method also includes detecting an operator touch and a location of the operator touch in the display area and moving the user-selectable element as directed by the operator according to the operator touch. The location indicator and the activating portion have fixed positions with respect to each other as the user-selectable element is moved by the operator. The user-selectable element is configured to operate in an activated state and in an inactivated state. The user-selectable element configured to modify the medical image when in the activated state.

In another embodiment, a diagnostic system is provided that includes a display area viewable by a user of the diagnostic system and configured to show a medical image and a user-selectable element thereon. The user-selectable element includes an activating portion and a location indicator. The diagnostic system also includes a display module that is configured to identify an operator touch and a location of the operator touch in the display area. The display module is configured to move the user-selectable element along the medical image in the display area as directed by the operator when the activating portion is touched. The user-selectable element is configured to operate in an activated state and in an inactivated state. The user-selectable element configured to modify the medical image when in the activated state. The diagnostic system also includes a marking module that is configured to at least one of (i) designate a track along a path of the location indicator as the location indicator is directed by the operator or (ii) designate a reference line on the medical image as directed by the operator through the location indicator.

DETAILED DESCRIPTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
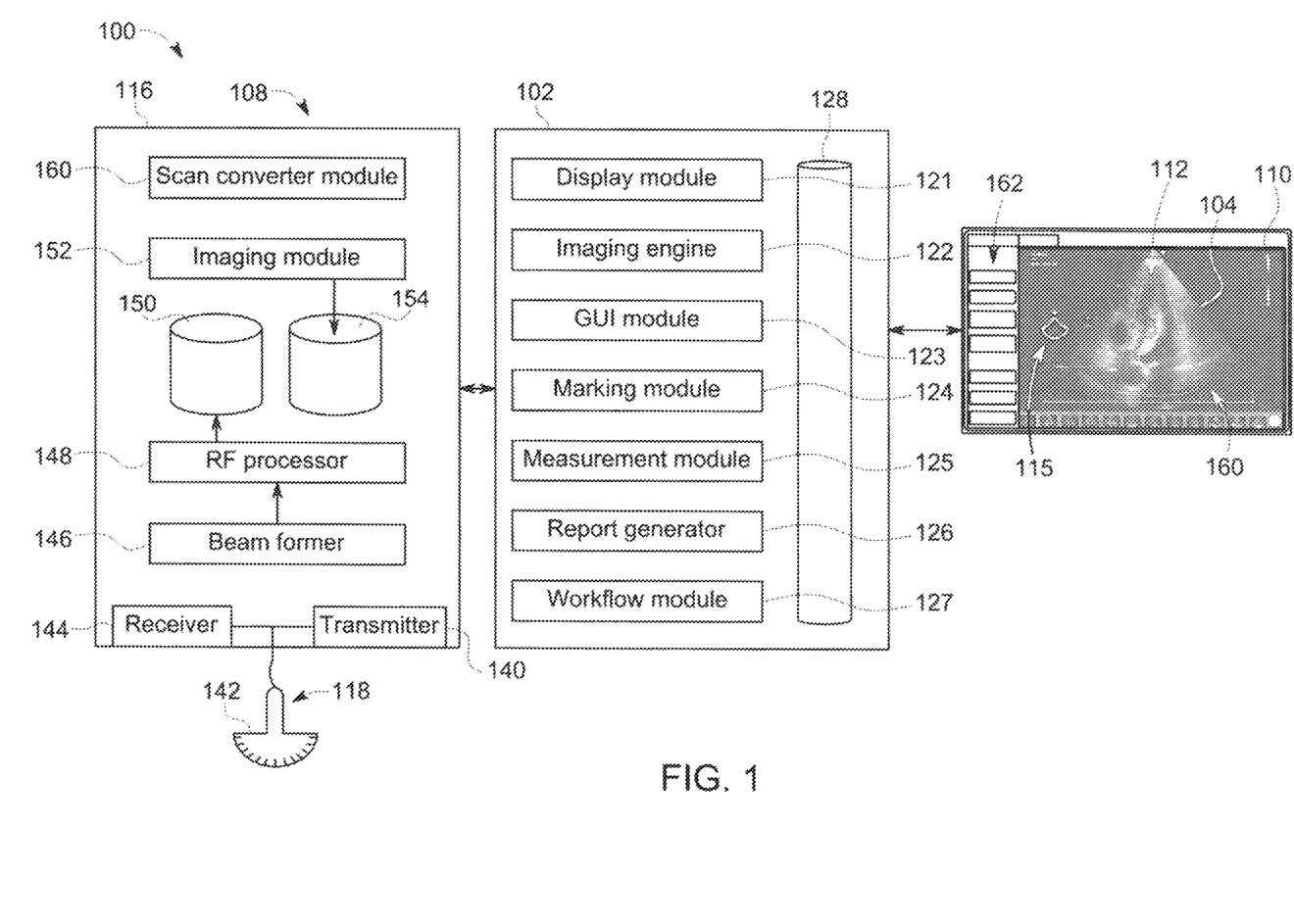
FIG. 1 is a block diagram of a diagnostic system formed in accordance with one embodiment.

FIG. 1 is a block diagram of a diagnostic system 100 formed in accordance with one embodiment. In the illustrated embodiment, the diagnostic system 100 is configured to obtain a medical image from a patient and enable an operator of the diagnostic system 100 to analyze or modify the medical image, such as by marking the medical image and/or obtaining measurements of features in the medical image. In other embodiments, however, the diagnostic system 100 may only enable the operator to analyze or modify the medical image. For example, the diagnostic system 100 may not be configured to obtain the medical image, but may, instead, receive the medical image through a communication network or from a storage device from a remote imaging system. The diagnostic system 100 includes a computing system 102, a user interface 104, and, optionally, an imaging system 108. The computing system 102 is communicatively coupled to the user interface 104 and the imaging system 108 and may be configured to control operation of the user interface 104 and the imaging system 108.

In an exemplary embodiment, the imaging system 108 is an ultrasound imaging system. However, the imaging system 108 may be a different modality in other embodiments. For example, the imaging system 108 may be a magnetic resonance imaging (MRI) system, a computer tomography (CT) system, a positron emission tomography (PET) system, a single photon emission computed tomography (SPECT) system, an x-ray imaging system, etc. In some cases, the imaging system 108 may be a multi-modality imaging system that includes more than one type of imaging modality, or the computing system 102 may be a workstation that is configured to review medical images from various modalities. Accordingly, embodiments described herein may utilize ultrasound medical images as well as medical images of other modalities.

In an exemplary embodiment, the computing system 102 includes one or more processors/modules configured to instruct the user interface 104 and the imaging system 108 to operate in a designated manner during, for example, a diagnostic session. The processors/modules may also receive inputs (e.g., commands, data, etc.) from the operator (or user) through the user interface 104 or other data from a remote system. The diagnostic session may include imaging the patient and/or analyzing the acquired medical image. The computing system 102 is configured to execute a set of instructions that are stored in one or more storage elements (e.g., instructions stored on a tangible and/or non-transitory computer readable storage medium) to control operation of the diagnostic system 100. The set of instructions may include various commands that instruct the computing system 102 as a processing machine to perform specific operations such as the workflows, processes, and methods described herein. In FIG. 1, the computing system 102 is indicated as a separate unit with respect to the user interface 104 and the imaging system 108. However, it is understood that computing system 102 is not necessarily separate from the user interface 104 and the imaging system 108. Instead, the computing system 102 may be distributed throughout the diagnostic system 100, such as in parts of the user interface 104 and/or the imaging system 108.

The user interface 104 may include hardware, firmware, software, or a combination thereof that enables an individual (e.g., an operator) to directly or indirectly control operation of the diagnostic system 100 and the various components thereof. For example, the user interface 104 may include the display module 121 describe below or another module of the computing system 102. As shown, the user interface 104 includes a touch-sensitive display unit 110 that has a display area 112. The display unit 110 is configured to show, among other things, a medical image 114 and a user-selectable element 115 in the display area 112. As described in greater detail below, the user interface 104 enables the operator of the diagnostic system 100 to mark (e.g. draw upon) the medical image 114 and/or obtain measurements of an object in the medical image 114. For example, the operator may position markings (e.g., traces, reference objects or lines, etc.) at designated locations in the display area 112 and/or may measure anatomical structures of a patient region-of-interest (ROI) that is shown in the medical image 114. It is understood that the ROI may be represented in a two-dimensional image frame or cine movie or in a three-dimensional image. In particular embodiments, the image frames shown in the display area 112 are two-dimensional and represent slices of the ROI.

The display unit 110 can detect a presence of a touch from an operator of the diagnostic system 100 and can also identify a location of the touch in the display area 112. The display unit 110 may also be capable of detecting multiple separate touches (simultaneously or concurrently) and their respective locations in the display area 112. The operator touch(es) may be applied by, for example, at least one of an individual's hand (with or without a particular glove), stylus, or the like. As such, the display unit 110 may receive inputs from the operator and may also communicate information to the operator through the display area 112. In some embodiments, the user interface 104 may also include other input devices (not shown), such as a physical keyboard, mouse, and/or touchpad.

The display area 112 may define an entirety of a visible area of the display unit 110. The display area 112 may be defined by an array of pixels that are illuminated in a designated manner by the computing system 102 to present information to the operator. In other embodiments, the display area 112 may be only a portion of the available visible area. In the illustrated embodiment, a portion of the display area 112 may define an image region or area 160 where the medical image 114 is shown and a utility region 162 (or non-image region) where the medical image 114 is not shown.

In the illustrated embodiment, the display area 112 is a two-dimensional surface. It is understood that when a graphical element, such as the user-selectable element 115, is described as being positioned over or described as moving along the medical image, the graphical element only appears as such. The pixels in the display area 112 of the display unit 110 are configured to provide this appearance. For example, when the user-selectable element 115 appears to be located over the medical image 114, the pixels in the display area 112 are instructed to change or modify the corresponding light intensities to provide the appearance that the user-selectable element 115 is located over the medical image 114. The pixels may also be configured to give the appearance that the user-selectable element 115 is partially transparent such that the medical image 114 is visible through the user-selectable element 115.

In the illustrated embodiment, the imaging system 108 includes a base unit 116 and an ultrasound probe or transducer 118. However, as described elsewhere, embodiments are not limited to the ultrasound modalities. The computing system 102, the user interface 104, and the imaging system 108 may be constructed into a single device or apparatus. For example, the computing system 102, the user interface 104, and the base unit 116 may be integrated into one component that is communicatively coupled to the probe 118. The integrated component may be similar to a tablet computer, a laptop computer, or desktop computer. In other words, the integrated component may be a portable device. This portable device may or may not be configured to communicatively couple to the probe 118. In some embodiments, the base unit 116, the computing system 102, and the user interface 104 may share a common housing. Alternatively, the diagnostic system 100 may include a plurality of separate components that may or may not be located near each other.

User-selectable elements may include visual elements that are displayed on a touch-sensitive display unit and, when touched by an operator, cause a programmed action or course to be taken by the computing system. The touches are detected by the computing system (e.g., a display module), which then commands one or more components in the system to perform specific operations. In some instances, the user selectable element may operate in different states, such as an activated state and an inactivated state. In the activated state, the user-selectable element may be configured to move along the medical image as directed by the operator. For example, the operator may slide his finger along a surface of the display unit or may touch a point on the display unit that causes the user-selectable element to move along the medical image.

In the activated state, the user-selectable element may modify (e.g., interact with) the medical image as directed by the operator. The modification can be a visible change to the medical image as viewed by the operator. For example, the modification may be a marking that overlays at least a portion of the ROI in the medical image. The user-selectable element may modify the medical image by overlaying a tracing or outline of a designated area or by overlaying a reference object onto the medical image. The tracing and the reference object may be stored with the medical image. It is noted that a medical image may be "modified" without permanently changing the medical image. For example, although the medical image may be stored with a tracing, the tracing can be later removed from the medical image or modified by another operator.

In the inactivated state, the user-selectable element may be capable of moving along the medical image as directed by the operator without modifying the medical image. The inactivated state may be used by the operator to position the user-selectable element at the desired location in the display area. At the desired location, the operator may then activate the user-selectable element so that the user-selectable element is in the activated state and is capable of modifying the medical image as described herein. The operator may activate the user-selectable element by performing a predetermined gesture. For example, the operator may provide one or more taps to the surface of the display unit at a designated location of the user-selectable element or at a designated location in the display area. Moreover, the user-selectable element may have different appearances in the different states. For example, the user-selectable element may change at least one of shape, color, light intensity, or size between the different states.

As used herein, the term "communicatively coupled" includes devices or components being electrically coupled to each other through, for example, wires or cables and also includes devices or components being wirelessly connected to each other such that one or more of the devices or components of the diagnostic system 100 may be located remote from the others. For example, the user interface 104 may be located at one location (e.g., hospital room or research laboratory) and the computing system 102 may be remotely located (e.g., central server system).

As used herein, the term "anatomical structure" may include an entire organ or system or may be an identifiable region or structure within the organ or system. In particular embodiments, the anatomical structures that are analyzed are structures of the heart. Examples of anatomical structures of the heart include, but are not limited to, the epicardium, endocardium, mid-myocardium, one or both atria, one or both ventricles, walls of the atria or ventricles, valves, a group of cardiac cells within a predetermined region of the heart, and the like. However, in other embodiments, anatomical structures may be structures found elsewhere in the body of the patient, such as other muscles or muscle systems, the nervous system or identifiable nerves within the nervous system, organs, and the like. It should also be noted that although the various embodiments may be described in connection with obtaining data related to a patient that is human, the patient may also be an animal.

The medical image may include an anatomical structure at a designated view that allows the operator to obtain measurements of the anatomical structure. For example, an ultrasound image of the heart may include a view of the heart when the heart is in a designated orientation with respect to the ultrasound probe. When the heart is in the designated orientation, one or more structural measurements of the heart may be determined from the corresponding ultrasound image. The structural measurements determined may include dimensions (e.g., thickness), volume, area, and the like. Other measurements may be computed from the structural measurements that are obtained from the ultrasound image(s).

The medical images may capture designated events of the anatomical structure, such as a designated cardiac-cycle event of the heart. As used herein, the term "designated cardiac-cycle event" may be an identifiable stage or moment in the cardiac cycle. In some cases, the stage or moment may occur when various structures of the heart have a relative position with respect to each other. For example, the stage or moment may occur when two walls have a greatest separation distance therebetween or a least separation distance therebetween (e.g., when a portion of the heart is contracted). As another example, the stage or moment may occur when a valve is fully opened or closed. In particular embodiments, the diagnostic system 100 is configured to measure one or more anatomical structures or features of the heart at a predetermined cardiac-cycle event.

In some embodiments, the imaging system 108 may include a transmitter 140 that drives an array of transducer elements 142 (e.g., piezoelectric crystals) within the probe 118 to emit pulsed ultrasonic signals into a body or volume. The pulsed ultrasonic signals may be for imaging a ROI that includes an anatomical structure, such as a heart. The ultrasonic signals are back-scattered from structures in the body, for example, adipose tissue, muscular tissue, blood cells, veins or objects within the body (e.g., a catheter or needle) to produce echoes that return to the transducer elements 142. The echoes are received by a receiver 144. The received echoes are provided to a beamformer 146 that performs beamforming and outputs an RF signal. The RF signal is then provided to an RF processor 148 that processes the RF signal. Alternatively, the RF processor 148 may include a complex demodulator (not shown) that demodulates the RF signal to form IQ data pairs representative of the echo signals. The RF or IQ signal data may then be provided directly to a memory 150 for storage (e.g., temporary storage).

The imaging system 108 may also include a processor or imaging module 152 to process the acquired image information and prepare image frames for display. In the case of ultrasound imaging systems, the acquired ultrasound information may include RF signal data or IQ data pairs. In an exemplary embodiment, the imaging module 152 is adapted to perform one or more processing operations according to a plurality of selectable ultrasound modalities on the acquired ultrasound information. Acquired ultrasound information may be processed in real-time during a diagnostic session as the echo signals are received. Additionally or alternatively, the ultrasound information may be stored temporarily in the memory 150 during a diagnostic session and processed in less than real-time in a live or off-line operation. An image memory 154 is included for storing processed frames of acquired ultrasound information that are not scheduled to be displayed immediately. The image memory 154 may comprise any known data storage medium, for example, a permanent storage medium, removable storage medium, etc.

The imaging module 152 is communicatively coupled to the user interface 104 that is configured to receive inputs from the operator to control operation of the imaging system 108. The display unit 110 may automatically display, for example, a 2D or 3D ultrasound data set stored in the memory 150 or 154 or currently being acquired. The data set may also be displayed with a graphical representation (e.g., a reference object). One or both of the memory 150 and the memory 154 may store 3D data sets of the ultrasound data, where such 3D data sets are accessed to present 2D and 3D images. For example, a 3D ultrasound data set may be mapped into the corresponding memory 150 or 154, as well as one or more reference planes. The processing of the data, including the data sets, may be based in part on operator inputs, for example, user selections received at the user interface 104.

In some embodiments, the ultrasound data may constitute IQ data pairs that represent the real and imaginary components associated with each data sample. The IQ data pairs may be provided to one or more image-processing modules (not shown) of the imaging module 152, for example, a color-flow module, an acoustic radiation force imaging (ARFI) module, a B-mode module, a spectral Doppler module, an acoustic streaming module, a tissue Doppler module, a C-scan module, and an elastography module. Other modules may be included, such as an M-mode module, power Doppler module, harmonic tissue strain imaging, among others. However, embodiments described herein are not limited to processing IQ data pairs. For example, processing may be done with RF data and/or using other methods.

As shown, the computing system 102 may include a plurality of modules or sub-modules that control operation of the diagnostic system 100. For example, the computing system 102 may include the modules 121-127 and a storage system 128 that communicates with at least some of the modules 121-127, the imaging system 108, and the user interface 104. As shown, the computing system 102 may also include an imaging engine 122 that may be configured to control operation of the imaging system 108. Also shown, the computing system 102 includes a display module 121 that is configured to detect an operator touch and a location of the operator touch in the display area 112. The display module 121 is also configured to move the user-selectable element 115 along the medical image 114 in the display area 112 as directed by the operator based on an operator input (e.g., the operator touch). The display module 121 may also be configured to at least one of (a) move the medical image 114 within the display area 112 as directed by the operator or (b) change a zoom level of the medical image 114 in the display area 112 as directed by the operator.

The graphical user interface (GUI) module 123 may coordinate with the other modules and the imaging system 108 for displaying various objects (e.g., medical images, user-selectable elements, tabs, frames, reference objects, etc.) by the display unit 110. For example, various graphical images of the user-selectable elements and the reference objects, described in greater detail below, may be stored in the storage system 128 and provided to the display unit 110 by the GUI module 123.

The computing system 102 also includes a workflow module 127. The workflow module 127 may be configured to respond to operator inputs during a diagnostic session or workflow of the diagnostic system 100 and instruct the user interface 104 to operate in a predetermined manner based on the operator inputs. For example, during a reference stage, activation of the user-selectable element may enable positioning of a reference line. During a tracing stage, activation of the user-selectable element may enable tracing of an anatomical structure.

A marking module 124 of the computing system 102 may be configured to mark the medical image. The marking may be any graphical structure or drawing that is not part of the original medical image and that is designated by the operator input. For example, a marking may include a line, a trace, a dot or point, a geometric figure (e.g., circle, square or other polygon, and the like), a cross-hair, an alphanumeric character, a symbol (e.g., a Greek or Latin letter), or a portion thereof. In some embodiments, the markings may be solid, dashed, or partially transparent. In particular embodiments, the marking includes a trace that extends along a path designated by the operator and/or a point or points of a reference line designated by the operator. The marking module 124 may be configured to at least one of (i) designate a trace along a path taken by the user-selectable element 115 as directed by the operator or (ii) designate a reference object on the medical image 114 as directed by the operator through the user-selectable element 115.

A measurement module 125 of the computing system 102 may be configured to analyze the medical image and a marking designated by the operator and determine a measurement therefrom. For example, the measurement module 125 may measure a distance between two points along a reference line that was designated by the operator.

The computing system 102 may also include a report generator 126. The report generator 126 may analyze measurements obtained by the imaging system 108 and provide a report that may or may not include a recommended diagnosis. As such, the report generator 126 may also be referred to as a diagnostic module. The analysis of the report generator 126 may include analyzing the measurements of the anatomical structure(s) in at least one of the medical images and other patient information. In some embodiments, the report generator 126 does not process or analyze the measurements, but simply generates a report that includes the measurements in a predetermined format. In some embodiments, the report is a virtual report stored in the diagnostic system 100.

Figure 2:
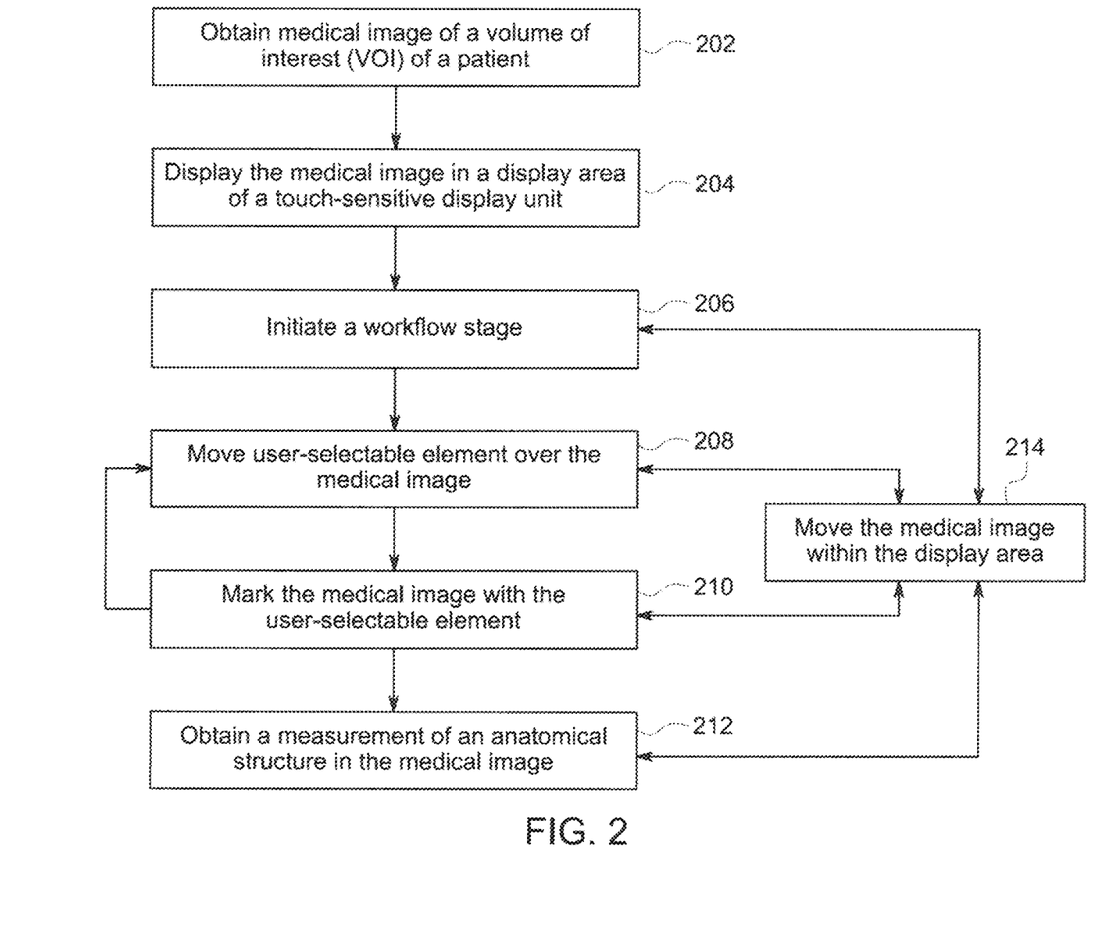
FIG. 2 is a flow chart that illustrates a workflow in accordance with one embodiment that may be performed with the diagnostic system of FIG. 1.

FIG. 2 is a flowchart illustrating a workflow or method 200 that may be referred to throughout the description of FIGS. 3-9. Although the workflow 200 shows numerous operations or steps that an operator may perform using a diagnostic system, embodiments described herein are not limited to performing each and every operation described herein and/or performing operations in the order shown in FIG. 2. Embodiments may also include operations that are not shown in FIG. 2.

The method 200 may include obtaining at 202 a medical image 302 that includes a ROI from an individual (e.g., patient). The medical image 302 may be obtained by acquiring the medical image 302 through an imaging system, such as the imaging system 108, or the medical image 302 may be retrieved from a storage system or retrieved remotely. For example, the computing system (e.g., the computing system 102) may be separate from an imaging system and, instead, may be configured to receive medical images from an image server that is connected to a plurality of imaging systems of the same or different modality. The computing system in this case may retrieve stored medical images 302 from the server in which the medical images were obtained days, weeks, months, etc., prior to the image analysis performed by the computing system.

In the illustrated embodiment, the medical image 302 is an ultrasound image. However, in other embodiments, the medical image 302 may be provided by another type of imaging modality as described herein. As used herein, the term medical image may include a single image frame or a plurality of image frames, including a series of image frames that form a continuous movie (e.g., cine movie). In some embodiments, the medical image may be acquired "as-is" by the imaging system. In other embodiments, the medical image may have undergone some post-processing. Moreover, the medical image can be 2D or 3D.

The medical image 302 may be displayed at 204 in a display area 304 of a touch-sensitive display unit 306. The display unit 306 may be similar to the display unit 110 (FIG. 1) described above and may be part of a user interface. The display unit 306 is configured to detect a touch from an operator (also referred to as an operator input) and detect a location of the touch in the display area 304.

The method 200 may also include initiating at 206 a workflow stage. In an exemplary embodiment, the workflow stages may include a first marking (or tracing) stage and a second marking (or reference) stage. As used herein, the user interface may be configured to operate in different designated manners during different workflow stages. For instance, the display module may be programmed to respond differently to the same gesture or touch of an operator for different workflow stages. As a specific example, during the tracing stage a "double-tap" input from the operator may activate a tracing feature in which a trace is designated along a path taken by the user-selectable element when moved by the operator. However, during the reference stage, the double-tap input may activate the user-selectable element to move one point indicator of a reference line for measuring an anatomical structure.

As described herein, each of the tracing and reference stages may include one or more operations of moving at 208 the user-selectable element; marking at 210 the medical image using the user-selectable element; moving at 214 the medical image 302 within the display area; or obtaining at 212 a measurement of an anatomical structure in the medical image. The moving operations at 208 and 214, the marking operation at 210, and the obtaining operation 212 are not required to be implemented in a particular order and more than one of each operation can be implemented. For example, the medical image 302 may be moved at 214 before moving at 208 the user-selectable element. After moving the user-selectable element through a portion of the medical image 302, the medical image 302 may then be moved again.

Figure 3:
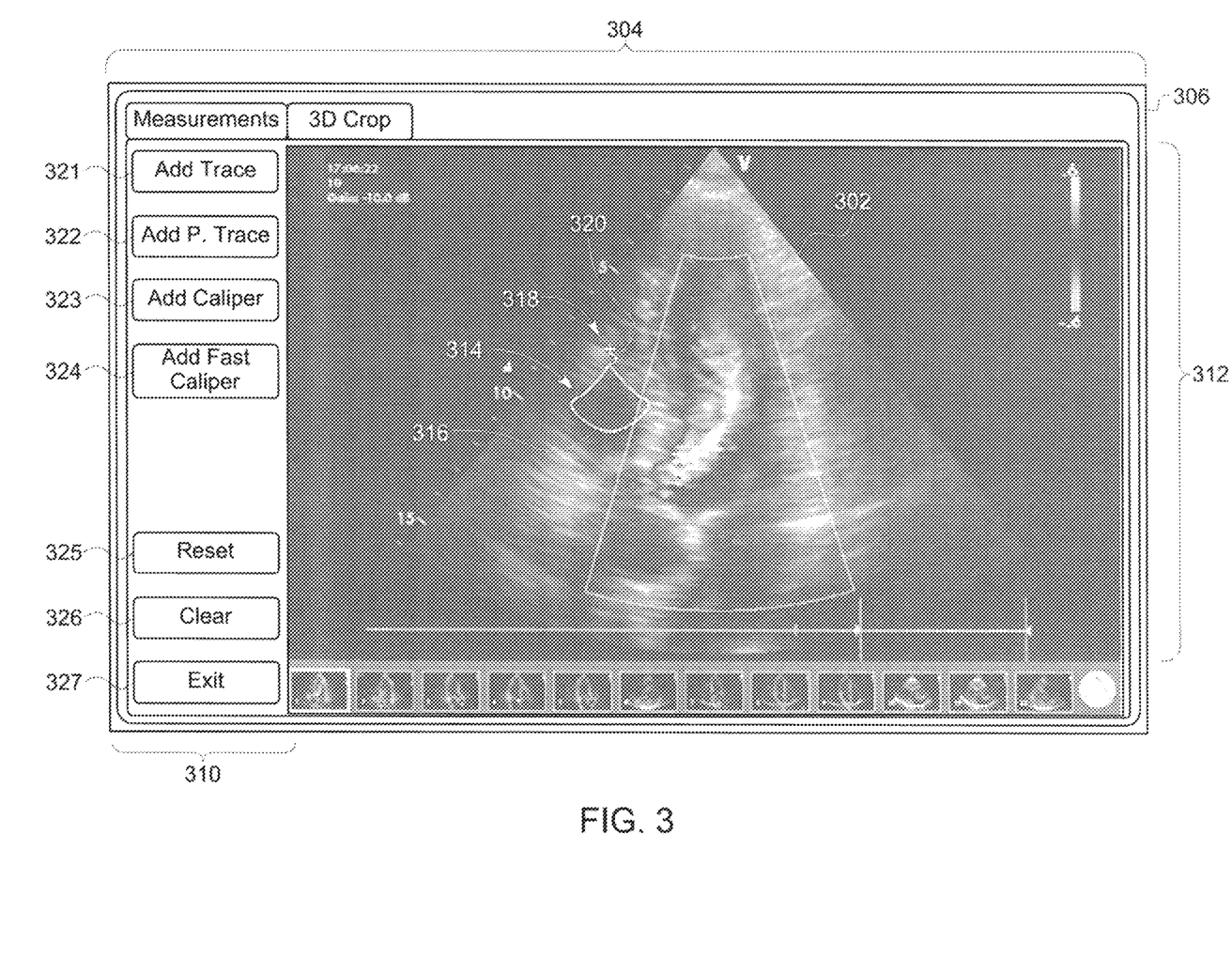
FIG. 3 shows an operative screen that may be displayed on a touch-sensitive display unit of the diagnostic system of FIG. 1.

FIG. 3 shows an exemplary display area 304 of the display unit 306. The display area 304 includes a utility section or sub-area 310 and an image section or sub-area 312. As shown in FIG. 3, the display area 304 may show a plurality of user-selectable elements that include buttons 321-327 in a portion of the utility section 310. The buttons may be activated (e.g., pressed by the operator) to transition between the different stages of a workflow. In the illustrated embodiment, the buttons 321-327 are respectively labeled: "Add Trace"; "Add P. Trace"; "Add Caliper"; "Add Fast Caliper"; "Reset"; "Clear"; and "Exit." The buttons 321 and 322 may be activated when it is desired to mark (e.g., trace) a portion of the medical image and, more specifically, an anatomical structure of the patient. The buttons 323 and 324 may be activated when it is desired to provide a reference object, such as a reference line on the medical image. The button 326 may be activated to clear any markings from the medical image. The button 327 may be activated to exit the workflow. In some embodiments, the buttons 321-327 may be activated at any time. For example, the operator is not required to follow a particular order of operations.

As shown in FIG. 3, the display unit 306 is configured to display the medical image 302 and a user-selectable element 314 in the display area 304. The user-selectable element 314 may be shown in the display area 304 when one of the workflow stages is activated. For example, one of the buttons 321-324 may be activated by the operator thereby causing the user-selectable element 314 to be shown to the operator in the image section 312. In the illustrated embodiment, the user-selectable element 314 includes an activating portion 316 and a location indicator 318. The activating portion 316 is sized and shaped to be touched by a finger of the operator or an operator stylus. Although the illustrated embodiment shows only a single user-selectable element 314, a plurality of user-selectable elements 314 may be used to modify or interact with the medical image 302 in other embodiments.

The user-selectable element 314 is configured to be activated by the operator and moved within the display area 304 (e.g., the image section 312) and along the medical image 302 as directed by the operator. After a workflow stage is initiated at 206, the user-selectable element 314 may be presented to the operator. The operator may activate the user-selectable element 314 by touching the activating portion 316. When the activating portion 316 is touched, the display area 304 may indicate to the operator that the user-selectable element 314 is in an activated state. For instance, the user-selectable element 314 may change in size (e.g., overall dimensions may increase or a thickness of the lines may increase). The user-selectable element 314 may also have a first color when not activated and a different, second color when inactivated. For example, the user-selectable element 314 may change from a yellow or white color to an orange color when activated.

The location indicator 318 indicates to the operator a precise point where the user-selectable element 314 may interact with the medical image 302. The location indicator 318 may be any identifiable structure or graphic that can be used by an operator to identify a desired point or area in the medical image and designate a marking on the medical image. As shown, the location indicator 318 includes crosshairs. In other embodiments, however, the location indicator 318 may be a dot or circle. The location indicator 318 may also be a corner or edge. In the illustrated embodiment, the activating portion 316 is defined by a border or boundary and resembles a shaped pad. The location indicator 318 may be separate from the activating portion 316.

The user-selectable element 314 is configured to be activated during different workflow stages to interact with or modify (e.g., mark) the medical image 302. However, the user-selectable element 314 may interact with the medical image 302 in different manners based on the workflow stage. For example, in the illustrated embodiment, the location indicator 318 indicates where a trace or line is being drawn by the user-selectable element 314 when the user-selectable element 314 is activated during a tracing stage. However, the location indicator 318 may indicate where a point (e.g., end) of a reference line is located with respect to the medical image 302 when the user-selectable element 314 is activated during a reference stage.

The location indicator 318 and the activating portion 316 may have fixed positions with respect to each other. More specifically, the location indicator 318 and the activating portion 316 may have fixed positions with respect to each other as the user-selectable element 314 is moved along the display area 304. As shown, the location indicator 318 may be located a separation distance 320 away from the activating portion 316 such that the location indicator 318 is visible to the operator as the user-selectable element 314 is moved by the operator. In such embodiments, although the activating portion 316 may be at least partially hidden by the operator's finger or tool, the location indicator 318 is viewable by the operator. During the moving operation 208, the operator may slide the finger or tool along a surface of the display area 304 to direct or guide the location indicator 318 along the medical image. The display unit 306 may provide a marking (e.g., trace or line) where the location indicator 318 is located at that time.

The marking operation 210 may include activating the user-selectable element 314 so that the user-selectable element 314 is in an activated state. The user-selectable element 314 may be activated when the display unit 306 detects a predetermined touch or gesture from the operator. The marking operation 210 may also include providing a trace along the medical image or providing a reference object on the medical image. In some cases, the marking operation 210 and the moving operation 208 occur simultaneously. For example, as the user-selectable element 314 is moved along the medical image 302, the tracing may be drawn by the location indicator 318.

The location indicator 318 and the activating portion 316 may be separate parts as shown in FIG. 3 or, alternatively, the location indicator 318 and the activating portion 316 may be part of a common structure. For example, the location indicator 318 may be a corner, edge, or end point of the activating portion 316. Nonetheless, the alternative location indicator 318 may be visible to the operator as the user-selectable element 314 is moved by the operator.

Figure 4:
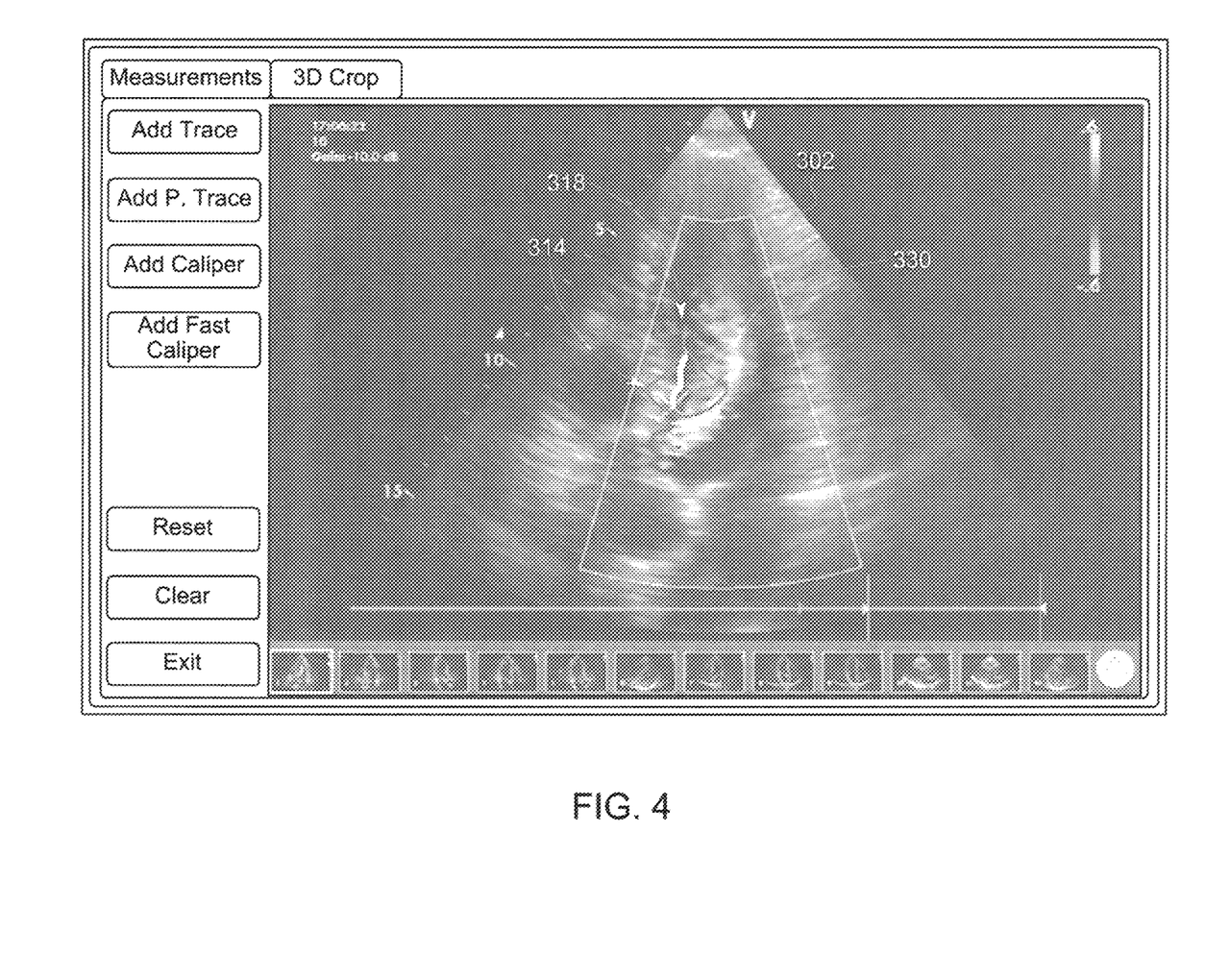
FIG. 4 shows the operative screen of FIG. 3 during a marking stage in which an anatomical feature is traced.
Figure 5:
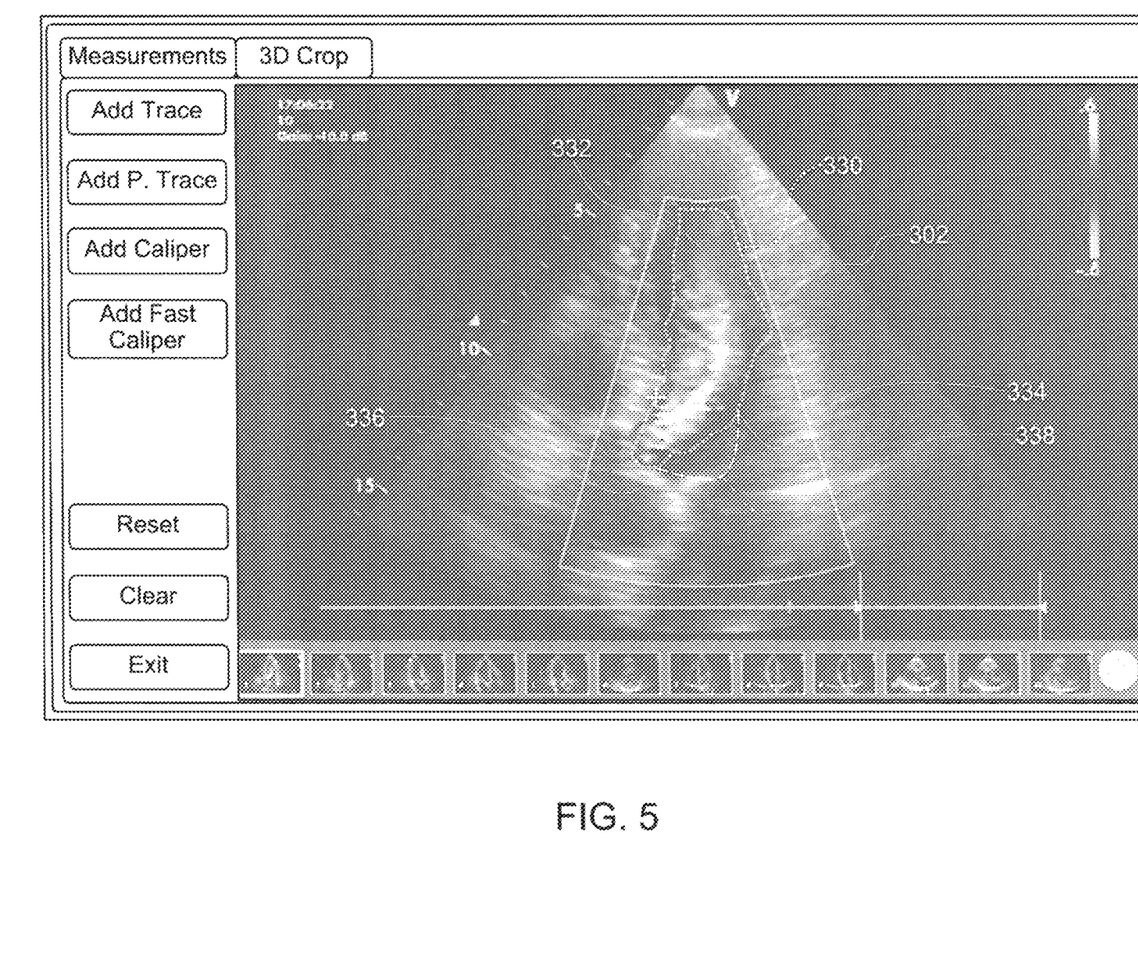
FIG. 5 shows the operative screen of FIG. 3 during the marking stage in which the anatomical feature has been completely traced.

FIGS. 4 and 5 illustrate a first marking stage (referred to as a tracing stage) of the workflow. While in the tracing stage, the operator is permitted to move the user-selectable element 314 along the medical image 302 while the user-selectable element 314 is activated or deactivated. To activate the user-selectable element 314 in the tracing stage, the operator may touch the display area 112 in a designated manner. For example, the operator may tap the activating portion 316 to activate the user-selectable element 314. When the user-selectable element 314 is in an activated state during the tracing stage, the location indicator 318 (FIG. 4) may mark a tracing 330 on the medical image 302. The tracing 330 is indicative of a path taken by the location indicator 318 as directed by the operator. Accordingly, during the tracing stage, the user-selectable element 314 (FIG. 4) may operate like an electronic pen that designates a tracing 330 over the medical image 302. When the user-selectable element 314 is not activated during the tracing stage (e.g., when in an inactivated state), the location indicator 318 may move along the medical image 302 without marking the medical image. As such, the user-selectable element can change from a "pen down" state in which the operator is enabled to draw upon the medical image and a "pen up" state in which the user-selectable element does not interact with the medical image.

FIG. 5 shows the medical image 302 after the tracing 330 has been completed. In the illustrated embodiment, the completed tracing 330 is a closed structure such that the tracing 330 encloses (e.g., surrounds or circumscribes) one section 332 of the medical image 302 and separates the section 332 from a remainder of the medical image 302. However, in other embodiments, the tracing 330 may not be a closed structure. For example, the tracing 330 may not join itself to separate a section of the medical image 302 from a remainder of the medical image 302.

After the operator has designated (e.g., drawn) the tracing 330 using the location indicator 318 (FIG. 4), the operator may deactivate the user-selectable element 314 (FIG. 4) by, for example, tapping the user-selectable element 314. In some embodiments, the user-selectable element 314 may disappear when deactivated by the operator after the tracing 330 is complete. If the tracing 330 is a closed structure as shown in FIG. 5, the user interface may be configured to calculate a measurement of the enclosed section 332. This calculation may be performed automatically immediately after the tracing 330 is completed or the operator may instruct the computing system to determine a designated measurement. For example, the measurement module 125 (FIG. 1) may automatically calculate an area of the enclosed section 332 as defined by the tracing 330 or a density of the anatomical structure in the medical image 302 that is defined within the enclosed section 332.

In some embodiments, if the tracing 330 is not completely enclosed, the user interface may automatically enclose the tracing 330 by joining two proximate ends of the tracing 330. For example, the operator may attempt to draw a closed structure by surrounding a portion of the medical image 302, but the tracing 330 does not join itself. In such cases, the computing system 102 may automatically join the two ends or may prompt the operator by asking if the operator would like the tracing 330 to enclose a section. After completing the tracing 330 thereby defining the section, the user interface may obtain a measurement of the section as described above.

In some embodiments, the computing system 102 may analyze the medical image 302 and suggest the tracing 330 that surrounds the designated anatomical structure. For example, the computing system 102 may analyze the medical image 302 (e.g., by segmenting and analyzing the light intensities of the pixels) and automatically determine where an anatomical structure is located. The operator may provide inputs that accept the suggested tracing 330, decline the suggested tracing 330, or correct the suggested tracing 330. To correct the suggested tracing 330, the operator may move the location indicator 318 off of the suggested tracing 330 from a first point indicator 334 on the suggested tracing 330. The operator may then move the location indicator 318 along a path (or tracing segment) 338 that is not on the suggested tracing 330 to a second point indicator 336 along the suggested tracing 330. The portion of the suggested tracing 330 between the first and second point indicators 334, 336 may then be erased and the tracing segment 338 provided by the operator may be added to the remainder of the suggested tracing 330.

In some embodiments, after the operator has designated the tracing 330, the operator may command the computing system (e.g., by activating one of the buttons alongside the display area) to refine the suggested tracing 330. For example, one of the modules (e.g., the marking module 124 or the measurement module 125) may analyze the pixels that are within a predetermined distance from the tracing 330. As one specific example only, the module may analyze the pixels that are at most 5 mm away from the tracing 330 on one side and the pixels that are at most 5 mm away from the tracing on the other side. The module may examine the light intensities to identify, for example, boundaries or borders of anatomical structure(s) that are near the tracing 330. The module may then modify the tracing 330 so that the tracing 330 more closely follows the identified boundary. Although this example relates to identifying a boundary of an anatomical structure, embodiments described herein are not limited to only identifying boundaries and, as such, the module may be configured to identify other designated features for refining the tracing 330.

Figure 6:
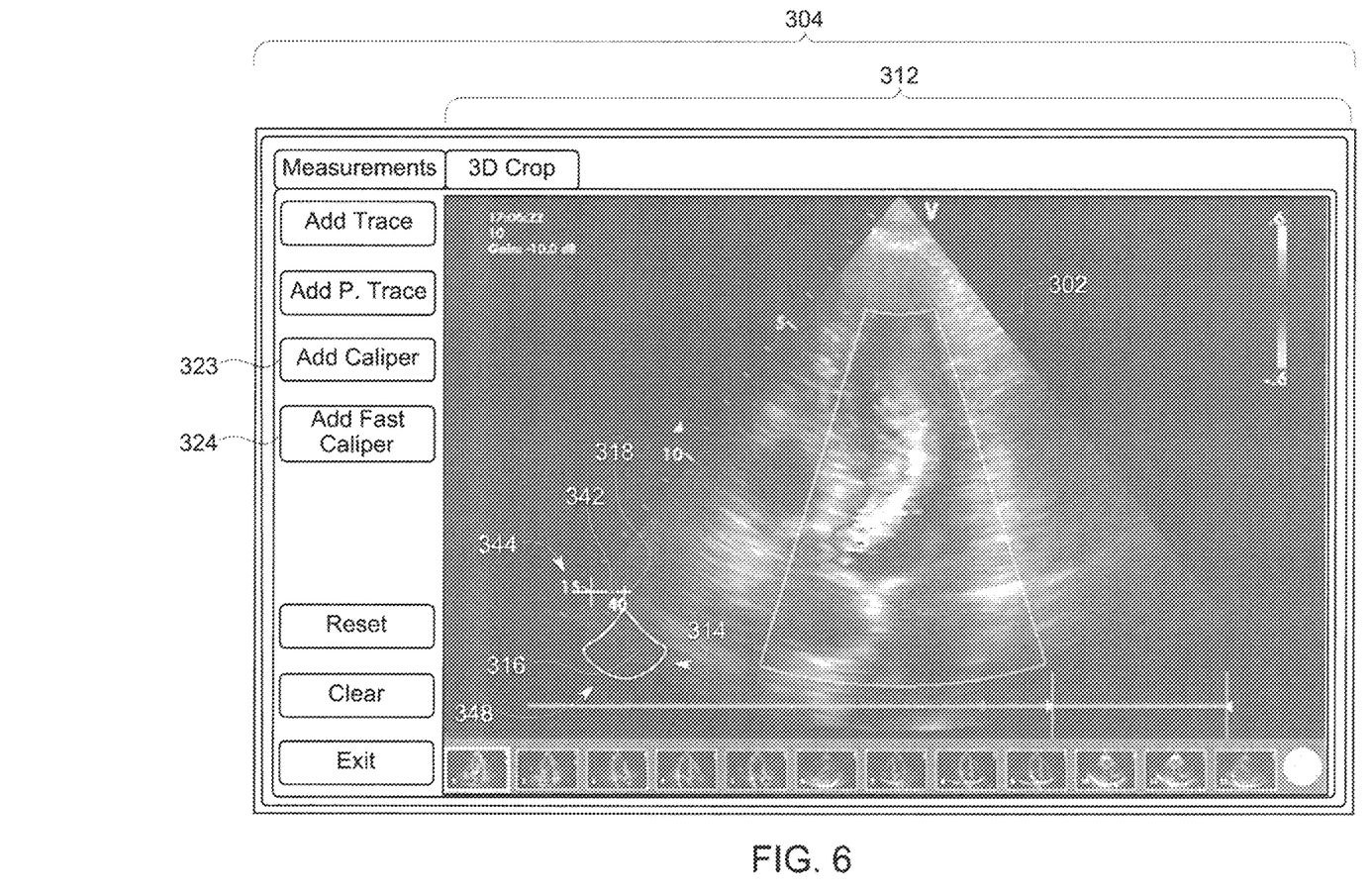
FIG. 6 shows the operative screen of FIG. 3 during a reference stage in which a first end of a reference line has been positioned.
Figure 7:
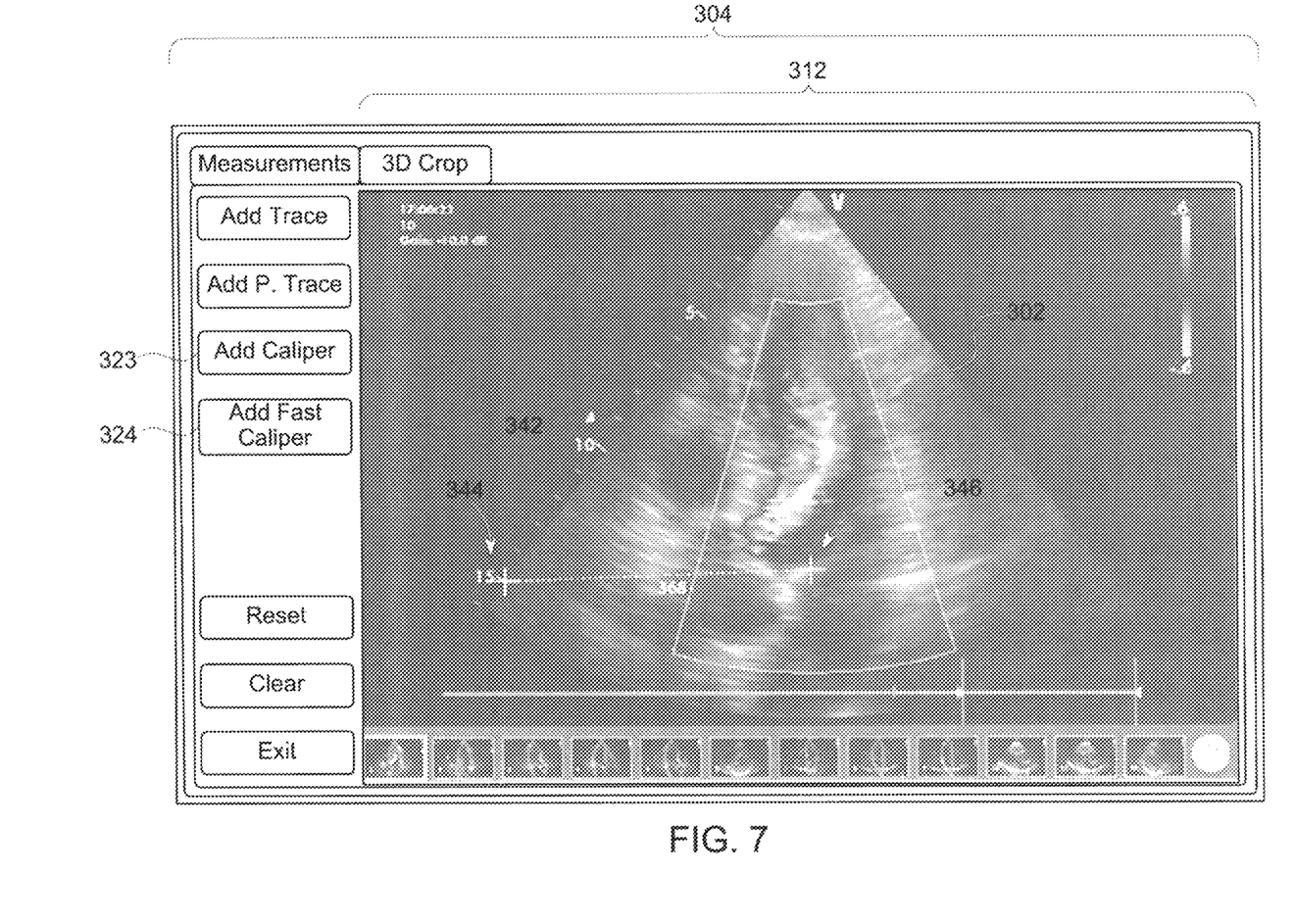
FIG. 7 shows the operative screen of FIG. 3 during the reference stage in which a second end of the reference line has been positioned.

FIGS. 6 and 7 illustrate a second marking stage (referred to as a reference stage) of the workflow. To initiate the reference stage, the operator may activate either of the buttons 323, 324. When the reference stage is initiated, the user-selectable element 314 may appear in the image section 312 of the display area 304. During the reference stage, the user-selectable element 314 may be moved at 208 over the medical image 302 to mark at 210 the medical image 302 with a reference object, which is indicated as a reference line 342 in FIGS. 6 and 7. The reference line 342 may extend between a first point indicator 344 and a second point indicator 346.

To designate the first point indicator 344, the operator may press the activating portion 316 thereby activating the user-selectable element 314. The operator may drag the location indicator 318 to designate a placement of the first point indicator 344 in the display area 304. In the illustrated embodiment, when the operator releases the user-selectable element 314 (e.g., removes his or her finger from the activating portion 316), the first point indicator 344 may appear at the present location of the location indicator 318. The first point indicator 344 is indicated by cross-hairs in FIGS. 6 and 7.

As shown in FIG. 6, in some embodiments, after the user-selectable element 314 is released the display unit 110 (FIG. 1) automatically provides the first point indicator 344 (e.g., cross-hairs) and shifts the user-selectable element 314 to an offset position 348 with respect to the first point indicator 344. The offset position 348 is proximate to the first point indicator 344. The operator may then press the activating portion 316 to move the location indicator 318 toward a location for the second point indicator 346 as shown in FIG. 7. As the location indicator 318 is moved toward this location, the reference line 342 may extend with the location indicator 318. When the operator has moved the location indicator 318 to the location where the operator would like the second point indicator 346 to be, the operator may release the user-selectable element 314 by removing his or her finger from the activating portion 316. Once removed, the second point indicator 346 (e.g., cross-hairs) may appear at the designated location as shown in FIG. 7. The reference line 342 extends between and includes the point indicators 344, 346. In alternative embodiments, the point indicators 344, 346 may be designated by tapping the activating portion 316 instead of releasing the activating portion 316.

In some embodiments, if the operator desired to move one of the point indicators 344, 346, the operator could activate the desired point indicator 344 or 346 thereby causing the user-selectable element 314 to appear having the location indicator 318 located at or proximate to the corresponding point indicator. For example, if the point indicators 344, 346 were cross-hairs as shown in FIG. 7, the operator may press one of the cross-hairs to identify the point indicator to move. The operator may then move the user-selectable element 314 that appears at or proximate to the selected point indicator to the desired position as described herein. Once the operator releases the activating portion 316, the re-located point indicator may appear at the new location.

Accordingly, in some embodiments, the point indicators 344, 346 may be characterized as user-selectable elements because the point indicators 344, 346 may be touched by the operator to activate a programmed operation, e.g., the user-selectable element 314 appearing next to the selected point indicator.

As shown in FIG. 7, the measurement module 125 is configured to display a value 350 to the operator regarding a measurement obtained using the reference line 342. For example, the value 350 may appear along the reference line 342 and may be indicative of a length or distance between the two point indicators. In some embodiments, as the reference line 342 is extended by moving one of the point indicators, the value 350 may be reconfigured to represent the new distance or length. In other embodiments, the value 350 is only configured after the point indicator is set.

In some embodiments, the user-selectable element 314 may operate in more than two states for a single stage. For example, the user-selectable element may be configured to operate in an inactivated state, a first activated, a second activated state, a third activated state, and so on. The first activated state may be similar to the tracing operation describes above, and the second activated state may be similar to the measurement operation described above. A third activated state may provide another tool that facilitates the operator's analysis (e.g., another measurement tool). The operator may instruct the computing system to move between different states by performing predetermined gestures or actions. For example, a double tap while in the inactivated state may change the state of the user-selectable element 341 to the first activated state. Another double tap may change the state of the user-selectable element 314 to the second activated state. In other embodiments, different gestures or actions may be performed to move between different states.

Figure 8:
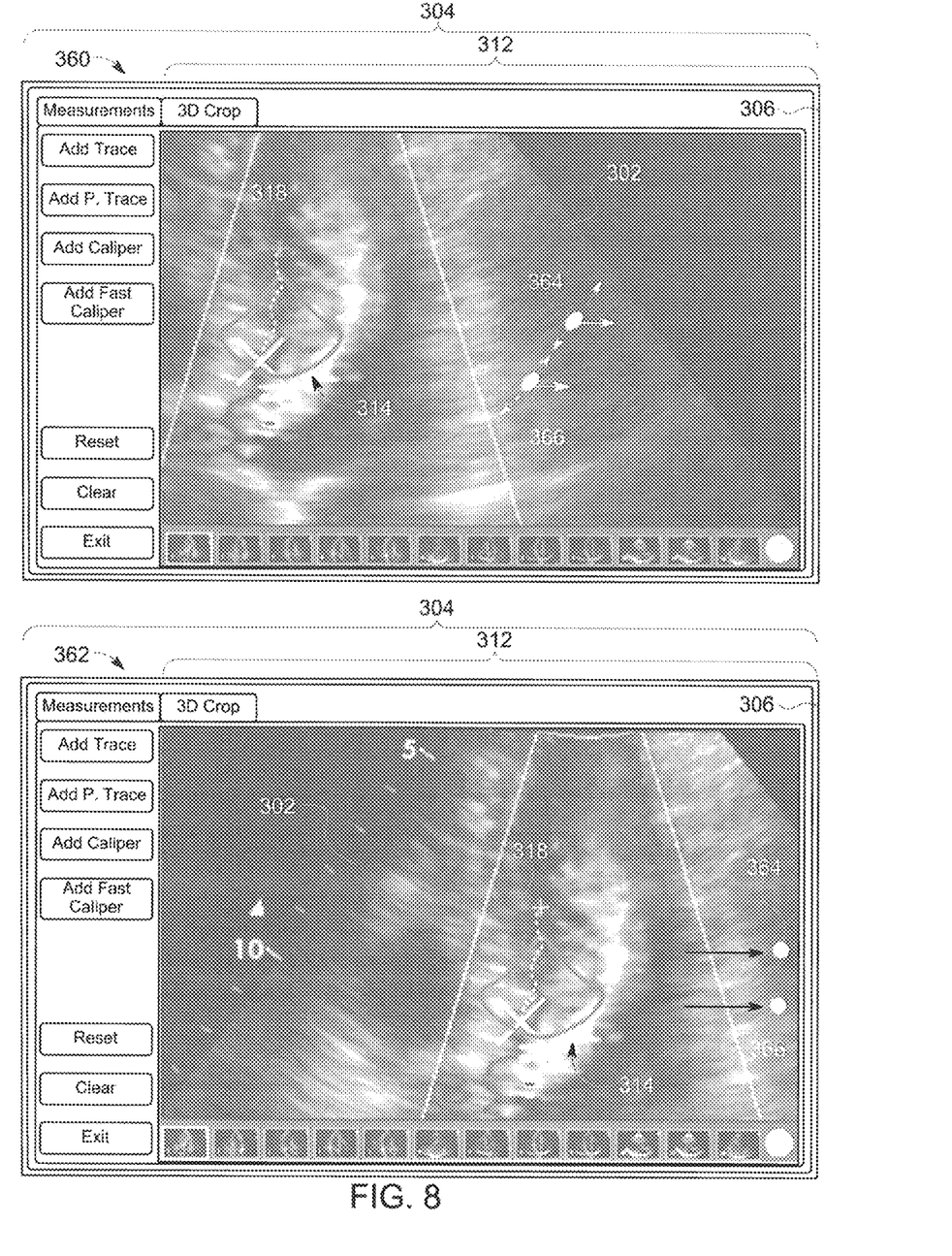
FIG. 8 shows two different views of the operative screen of FIG. 3 illustrating movement of the medical image.

FIG. 8 illustrates two different views 360, 362 of the display unit 306 illustrating how the medical image 302 may be moved within the display area 304. More particularly, the medical image 302 has been moved within the image section 312 of the display area 304. Embodiments described herein may enable the operator to move the medical image 302 by (a) changing a zoom level and/or (b) shifting the medical image laterally (e.g., along a plane of the display area 304).

In FIGS. 3-7, the medical image 302 is at a first zoom level. However, the medical image 302 is at an enlarged second zoom level in FIG. 8. To change the zoom level of the medical image 302, the operator may provide designated inputs through the user interface. In particular embodiments, the operator may touch the display area 304 in a predetermined manner to change the zoom level. For example, the operator may touch the image section 312 at two spaced-apart points 364, 366. Although the points 364, 366 are shown at particular locations in FIG. 8, the points 364, 366 may have other locations within the image section 312. More specifically, the points 364, 366 are not necessarily required to be within a certain distance of each other or within a certain portion of the image section 312. To enlarge the medical image 302 (e.g., increase the zoom level), the operator may slide his or her fingers away from each other such that the points 364, 366 move away from each other. To shrink the medical image (e.g., decrease the zoom level), the operator may slide his or her fingers toward each other such that the points 364, 366 move toward each other. The display module 121 detects the movements of the touches toward or away from each other and instructs the medical image 302 to move accordingly.

To laterally move the medical image 302 within the display area 304, the operator may touch the surface of the display unit 306 at the two spaced-apart points 364, 366 (or at two or more other points) and slide his or her fingers in a common direction along the surface of the display unit 306 as indicated in FIG. 8. The display module 121 detects the parallel movement of the touches and instructs the medical image 302 to laterally move in the same direction.

The moving at 214 of the medical image 302 may occur in either of the tracing or reference stages. For example, the operator may pause moving the user-selectable element 314 during the tracing stage and then engage the surface of the display unit 306 at separate points to laterally move and/or change the zoom level of the medical image 302. During movement of the medical image 302, the user-selectable element 314 may remain in a fixed position with respect to the medical image 302. In other words, the user-selectable element 314 may move with the medical image 302. In particular, the location of the location indicator 318 in the medical image 302 relative to an anatomical structure may remain the same during movement of the medical image 302. In some embodiments, the user-selectable element 314 may remain at the same size and shape even though the zoom level of the medical image 302 is changed.

After any one of the operations 208, 210, 212, 214, the operator may provide an operator input that commands the computing system 102 to store the display area 304 or the medical image 302. In some cases, these modified medical images 302 may be shown in thumbnails in the display area 304. For example, the thumbnails of other medical images 302 are shown along a bottom of the display area 304 in FIGS. 3-8. As such, the system 100 may be capable of storing medical images that have tracings, reference lines, and/or measurements indicated on the medical images in, for example, the storage system 128. An operator may then retrieve the stored medical images at a later time and, in some embodiments, may revise the tracings and/or reference objects and obtain new measurements. As described above, embodiments described herein are not limited to ultrasound images. Medical images from other modalities may be modified in an identical or similar manner.

It should be noted that FIGS. 3-9 merely illustrate one example of embodiments described herein in which a heart is imaged and dimensions of the different structures in the heart are determined. However, other anatomical systems, organs, or structures of a patient body may be analyzed to determine measurements thereof. Moreover, in alternative embodiments, the reference object may be other geometric shapes other than a line that an operator may use as a reference or standard for obtaining measurements of anatomical structures.

A technical effect of the various embodiments of the systems and methods described herein include user-friendly interfaces for obtaining measurements of an anatomical structure(s) in a patient using a touch-sensitive display unit. Another technical effect may include user-friendly interfaces for marking medical images using a display unit. Other technical effects may be provided by the embodiments described herein.

As described above, the various components and modules described herein may be implemented as part of one or more computers or processors. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor. The instructions may be stored on a tangible and/or non-transitory computer readable storage medium coupled to one or more servers.

As used herein, the term "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program may be compiled to run on both 32-bit and 64-bit operating systems.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

In other embodiments, a tangible non-transitory computer readable medium, excluding signals, is provided that is programmed to instruct a computing system to perform the method embodiments described herein. For example, the computing system may be instructed to display a medical image in a display area of the display unit and a user-selectable element. The user-selectable element may include an activating portion and a location indicator. The user-selectable element may be configured to move along the medical image when the activating portion is touched and directed by the operator. The computing system may also be instructed to move the user-selectable element as directed by the operator according to an operator touch. The location indicator and the activating portion may have fixed positions with respect to each other as the user-selectable element is moved by the operator. The location indicator may be located a distance away from the activating portion such that the location indicator is visible to the operator as the user-selectable element is moved by the operator.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

This written description uses examples to disclose the inventive subject matter, including the best mode, and also to enable any person skilled in the art to practice the inventive subject matter, including making and using any devices or systems and performing any incorporated methods. The patentable scope of the inventive subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A user interface comprising a touch-sensitive display that has a display area, the touch-sensitive display being configured to show a medical image and a user-selectable element in the display area, the display area having a two-dimensional image region where the medical image is shown, the touch-sensitive display being configured to detect an operator touch and detect a location of the operator touch in the image region of the display area, the user-selectable element comprising an activating portion and a location indicator, the touch-sensitive display being configured to move the user-selectable element along the medical image as directed by the operator when the activating portion is touched, the location indicator and the activating portion having fixed positions with respect to each other as the activating portion is directed by the operator along the display area such that the location indicator and the activating portion appear to move simultaneously in a same direction along the display area, wherein the user-selectable element is configured to operate in an activated state and in an inactivated state, the user-selectable element configured to modify the medical image when in the activated state.

2. The user interface of claim 1, wherein a fixed separation distance exists between the location indicator and a border of the activating portion and is maintained as the activating portion is directed by the operator.

3. The user interface of claim 1, wherein the activating portion and the location indicator are different portions of a common structure, the location indicator configured to be visible to the operator when the activating portion is touched by a finger of the operator or an operator stylus.

4. The user interface of claim 1, wherein the user-selectable element has a shape, the shape including the location indicator and the activating portion, the shape being maintained and unchanged as the user-selectable element moves along the display area.

5. The user interface of claim 1, wherein the touch-sensitive display is configured to operate in a marking stage, the location indicator appearing to mark a trace along a path of the location indicator when in the marking stage as the location indicator is directed by the operator.

6. The user interface of claim 1, wherein the touch-sensitive display is configured to operate in different first and second marking stages, the location indicator marking the medical image when activated in either of the first and second marking stages, wherein the location indicator marks the medical images in a different manner when in the first marking stage than when in the second marking stage.

7. The user interface of claim 1, wherein the touch-sensitive display is configured to operate in a marking stage, the location indicator configured to designate a point indicator along a reference line when the user-selectable element is activated by the operator.

8. The user interface of claim 1, wherein the medical image is permitted to move within the display area when directed by the operator, the location indicator having a fixed position relative to the medical image as the medical image is moved within the display area.

9. The user interface of claim 1, wherein the operator is enabled to change the medical image from a first zoom level to a second zoom level in the image region of the display area, the location indicator having a common location relative to a feature in the medical image at the first and second zoom levels.

10. A method of using a touch-sensitive display having a two-dimensional touch-sensitive surface, the method comprising:
displaying a medical image and a user-selectable element on the touch-sensitive surface of the touch-sensitive display, the user-selectable element comprising an activating portion and a location indicator, the user-selectable element being configured to move along the medical image when the activating portion is touched on the touch-sensitive surface and directed by the operator; and
moving the user-selectable element as directed by the operator when touching the touch-sensitive surface, the location indicator having a fixed position relative to the activating portion as the activating portion is directed by the operator along the touch-sensitive surface such that the location indicator and the activating portion appear to move simultaneously in a same direction along the touch-sensitive surface, wherein the user-selectable element is configured to operate in an activated state and in an inactivated state, the user-selectable element configured to modify the medical image when in the activated state.

11. The method of claim 10, wherein the location indicator is located a distance away from the activating portion such that the location indicator is visible to the operator on the touch-sensitive surface as the user-selectable element is moved by the operator.

12. The method of claim 10, wherein the activating portion is sized and shaped to be touched by a finger of the operator or an operator stylus, the location indicator configured to be visible to the operator while the activating portion is touched by the finger or the operator stylus.

13. The method of claim 10, further comprising marking the medical image on the touch-sensitive surface using the location indicator of the user-selectable element.

14. The method of claim 10, further comprising marking a trace along a path taken by the location indicator as the location indicator is directed by the operator.

15. The method of claim 10, further comprising, while the user-selectable element is in a fixed position relative to the medical image, at least one of (i) laterally moving the medical image along the touch-sensitive surface or (ii) changing a zoom level of the medical image from a first zoom level to a second zoom level.

16. A diagnostic system comprising:
a two-dimensional touch-sensitive surface viewable by an operator of the diagnostic system; and
one or more processors and a storage medium that is configured to store programmed instructions accessible by the one or more processors, wherein the one or more processors are configured to:
display a medical image and a user-selectable element on the touch-sensitive surface, the user-selectable element comprising an activating portion and a location indicator, the user-selectable element configured to operate in an activated state and in an inactivated state;
move the user-selectable element as directed by the operator when touching the touch-sensitive surface, the location indicator having a fixed position relative to the activating portion as the activating portion is directed by the operator along the touch-sensitive surface such that the location indicator and the activating portion appear to move simultaneously in a same direction along the medical image; and
modify the medical image when the user-selectable element is in the activated state.

17. The diagnostic system of claim 16, wherein the location indicator is located a distance away from the activating portion such that the location indicator is visible to the operator as the user-selectable element is moved by the operator.

18. The diagnostic system of claim 16, wherein the one or more processors are configured to at least one of (a) laterally move the medical image along the touch-sensitive surface as directed by the operator or (b) change a zoom level of the medical image, the location indicator having a fixed location on the medical image during (a) or (b).

19. The diagnostic system of claim 16, wherein the one or more processors are configured to modify the medical image by at least one of (i) designating a track along a path of the location indicator as the user-selectable element is directed by the operator in the activated state or (ii) designating a reference line on the medical image as directed by the operator through the location indicator when the user-selectable element is in the activated state.

20. The diagnostic system of claim 16, wherein the activating portion changes in at least one of shape, color, light intensity, or size when changing from the inactivated state to the activated state.

* * * * *